(12) United States Patent
Ishida

(10) Patent No.: US 10,383,997 B2
(45) Date of Patent: *Aug. 20, 2019

(54) INDWELLING ASSEMBLY

(71) Applicant: Terumo Kabushiki Kaisha, Shibuya-ku, Tokyo (JP)

(72) Inventor: Masahiro Ishida, Tokyo (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/156,253

(22) Filed: Oct. 10, 2018

(65) Prior Publication Data

US 2019/0038832 A1    Feb. 7, 2019

Related U.S. Application Data

(63) Continuation of application No. 15/616,299, filed on Jun. 7, 2017, which is a continuation of application (Continued)

(30) Foreign Application Priority Data

Mar. 26, 2010 (JP) .................. 2010-073414
May 28, 2010 (JP) .................. 2010-122413

(51) Int. Cl.
*A61M 25/06* (2006.01)
*A61M 5/158* (2006.01)

(52) U.S. Cl.
CPC ........ *A61M 5/158* (2013.01); *A61M 25/0606* (2013.01); *A61M 2005/1585* (2013.01); *A61M 2005/1587* (2013.01)

(58) Field of Classification Search
CPC .............. A61M 25/0606; A61M 5/158; A61M 2005/1585; A61M 2005/1587
See application file for complete search history.

(56) References Cited

U.S. PATENT DOCUMENTS

| 561,059 A | 5/1896 | Mitchell et al. |
| 2,705,949 A | 8/1953 | Silverman |

(Continued)

FOREIGN PATENT DOCUMENTS

| JP | 3-75748 U | 7/1991 |
| JP | 3-75749 U | 7/1991 |

(Continued)

OTHER PUBLICATIONS

International Search Report (PCT/ISA/210) dated Jun. 26, 2011, by the Japan Patent Office as the International Searching Authority for International Application No. PCT/JP2011/057010.

*Primary Examiner* — Theodore J Stigell
(74) *Attorney, Agent, or Firm* — Buchanan Ingersoll & Rooney PC

(57) ABSTRACT

An indwelling assembly includes an inner needle having a sharp needlepoint, an inner needle hub fixed to the inner needle, a hollow elongated outer member in which the inner needle is positioned and movable in a distal direction relative to the inner needle after puncturing the blood vessel to position the elongated outer member at a desired position in the blood vessel, an outer member hub fixed to hollow elongated outer member, a projection removably connected to the outer member hub and configured to be engaged by a finger of the user to apply a force to the projection causing the outer member hub and the hollow elongated outer member to move together with the projection in the distal direction relative to the inner needle and the inner needle hub, and an elongated movable member that is movable relative to the hollow elongated outer member and the outer member hub.

16 Claims, 14 Drawing Sheets

Related U.S. Application Data

No. 15/083,943, filed on Mar. 29, 2016, now Pat. No. 9,700,671, which is a continuation of application No. 14/583,410, filed on Dec. 26, 2014, now Pat. No. 9,352,128, which is a continuation of application No. 14/497,364, filed on Sep. 26, 2014, now Pat. No. 9,265,915, which is a continuation of application No. 13/627,385, filed on Sep. 26, 2012, now Pat. No. 8,876,773, which is a continuation of application No. PCT/JP2011/057010, filed on Mar. 23, 2011.

(56) References Cited

U.S. PATENT DOCUMENTS

| | | |
|---|---|---|
| 2,847,995 A | 8/1958 | Adams |
| 3,225,762 A | 12/1965 | Guttman |
| 3,352,306 A | 11/1967 | Hirsch |
| 3,358,684 A | 12/1967 | Marshall |
| 3,463,152 A | 8/1969 | Sorenson |
| 3,509,880 A | 5/1970 | Guttman |
| 3,536,073 A | 10/1970 | Farb |
| 3,584,624 A | 6/1971 | de Ciutiis |
| 3,630,195 A | 12/1971 | Santomieri |
| 3,834,380 A | 9/1974 | Boyd |
| 4,108,175 A | 8/1978 | Orton |
| 4,160,450 A | 7/1979 | Doherty |
| 4,194,504 A | 3/1980 | Harms et al. |
| 4,231,367 A | 11/1980 | Rash |
| 4,249,541 A | 2/1981 | Pratt |
| 4,311,137 A | 1/1982 | Gerard |
| 4,327,722 A | 5/1982 | Groshong et al. |
| 4,353,369 A | 10/1982 | Muetterties et al. |
| 4,362,156 A | 12/1982 | Feller, Jr. et al. |
| 4,392,856 A | 7/1983 | Lichtenstein |
| 4,431,426 A | 2/1984 | Groshong et al. |
| 4,439,583 A | 3/1984 | Gould et al. |
| 4,500,312 A | 2/1985 | McFarlane |
| 4,525,157 A | 6/1985 | Vaillancourt |
| 4,529,399 A | 7/1985 | Groshong et al. |
| 4,549,879 A | 10/1985 | Groshong et al. |
| 4,559,046 A | 12/1985 | Groshong et al. |
| 4,588,398 A | 5/1986 | Daugherty et al. |
| 4,627,841 A | 12/1986 | Dorr |
| 4,631,057 A | 12/1986 | Mitchell |
| 4,664,653 A | 5/1987 | Sagstetter et al. |
| 4,664,654 A | 5/1987 | Strauss |
| 4,668,225 A | 5/1987 | Russo et al. |
| 4,671,795 A | 6/1987 | Mulchin |
| 4,671,796 A | 6/1987 | Groshong et al. |
| 4,676,783 A | 6/1987 | Jagger et al. |
| 4,684,369 A | 8/1987 | Wildemeersch |
| 4,690,675 A | 9/1987 | Katz |
| 4,701,166 A | 10/1987 | Groshong et al. |
| 4,702,738 A | 10/1987 | Spencer |
| 4,728,322 A | 3/1988 | Walker et al. |
| 4,747,831 A | 5/1988 | Kulli |
| 4,762,516 A | 8/1988 | Luther et al. |
| 4,770,655 A | 9/1988 | Haber et al. |
| 4,772,264 A | 9/1988 | Cragg |
| 4,772,276 A | 9/1988 | Wiita et al. |
| 4,773,901 A | 9/1988 | Norton |
| 4,778,453 A | 10/1988 | Lopez |
| 4,781,692 A | 11/1988 | Jagger et al. |
| 4,798,597 A | 1/1989 | Vaillancourt |
| 4,826,490 A | 5/1989 | Byrne et al. |
| 4,828,549 A | 5/1989 | Kvalo |
| 4,832,696 A | 5/1989 | Luther et al. |
| 4,834,718 A | 5/1989 | McDonald |
| 4,846,799 A | 7/1989 | Tanaka et al. |
| 4,846,812 A | 7/1989 | Walker et al. |
| 4,863,432 A | 9/1989 | Kvalo |
| 4,887,998 A | 12/1989 | Martin et al. |
| 4,895,564 A | 1/1990 | Farrell |
| 4,898,591 A | 2/1990 | Jang et al. |
| 4,911,691 A | 3/1990 | Aniuk et al. |
| 4,917,671 A | 4/1990 | Chang |
| 4,927,415 A | 5/1990 | Brodsky |
| 4,944,728 A | 7/1990 | Carrell et al. |
| 4,950,252 A | 8/1990 | Luther et al. |
| 4,955,863 A | 9/1990 | Walker et al. |
| 4,973,313 A | 11/1990 | Katsaros et al. |
| 4,976,704 A | 12/1990 | McLees |
| 4,986,814 A | 1/1991 | Burney et al. |
| 4,994,046 A | 2/1991 | Wesson et al. |
| 4,998,919 A | 3/1991 | Schnepp-Pesch et al. |
| 5,002,533 A | 3/1991 | Jullien |
| 5,037,402 A | 8/1991 | Bartman |
| 5,047,018 A | 9/1991 | Gay et al. |
| 5,112,312 A | 5/1992 | Luther |
| 5,120,317 A | 6/1992 | Luther |
| 5,135,502 A | 8/1992 | Koenig, Jr. et al. |
| 5,147,332 A | 9/1992 | Moorehead |
| 5,199,947 A | 4/1993 | Lopez et al. |
| 5,205,829 A | 4/1993 | Lituchy |
| 5,273,540 A | 12/1993 | Luther et al. |
| 5,364,374 A | 11/1994 | Morrison et al. |
| 5,403,283 A | 4/1995 | Luther |
| 5,569,217 A | 10/1996 | Luther |
| 5,873,864 A | 2/1999 | Luther et al. |
| 6,482,180 B2 | 11/2002 | Toyokawa et al. |
| 8,876,773 B2 | 11/2014 | Ishida |
| 9,180,276 B2 | 11/2015 | Ishida |
| 9,186,483 B2 * | 11/2015 | Ishida ................ A61M 5/158 |
| 9,265,915 B2 | 2/2016 | Ishida |
| 9,352,128 B2 * | 5/2016 | Ishida ................ A61M 5/158 |
| 9,511,207 B2 * | 12/2016 | Ishida ................ A61M 5/158 |
| 9,561,325 B2 * | 2/2017 | Ishida ................ A61M 5/158 |
| 9,700,671 B2 * | 7/2017 | Ishida ................ A61M 5/158 |
| 2003/0220612 A1 | 11/2003 | Hiejima |
| 2008/0082052 A1 | 4/2008 | Schnell et al. |
| 2009/0036836 A1 | 2/2009 | Nystrom et al. |
| 2009/0105651 A1 | 4/2009 | Wada et al. |

FOREIGN PATENT DOCUMENTS

| | | | |
|---|---|---|---|
| JP | 10-503094 A | | 3/1998 |
| JP | 2002-28246 | * | 1/2002 |
| JP | 2002-28246 A | | 1/2002 |
| JP | 2003-339858 A | | 12/2003 |
| JP | 2009-142492 A | | 7/2009 |
| JP | 2009-232916 A | | 10/2009 |
| WO | 2006/090637 A1 | | 8/2006 |
| WO | 2007/098355 A1 | | 8/2007 |

* cited by examiner

INDWELLING ASSEMBLY

CROSS REFERENCES TO RELATED APPLICATIONS

This application is a continuation of U.S. application Ser. No. 15/616,299 filed Jun. 7, 2017, now U.S. Pat. No. 10,188,790, which is a continuation of U.S. application Ser. No. 15/083,943 filed Mar. 29, 2016, now U.S. Pat. No. 9,700,671, which is a continuation of U.S. application Ser. No. 14/583,410 filed Dec. 26, 2014, now U.S. Pat. No. 9,352,128, which is a continuation of U.S. application Ser. No. 14/497,364 filed Sep. 26, 2014, now U.S. Pat. No. 9,265,915, which is a continuation of U.S. application Ser. No. 13/627,385 filed Sep. 26, 2012, now U.S. Pat. No. 8,876,773, which is a continuation of International Application No. PCT/JP2011/057010 filed on Mar. 23, 2011, and claims priority to Japanese Patent Application No. 2010-073414 filed on Mar. 26, 2010 and Japanese Patent Application No. 2010-122413 filed on May 28, 2010, the entire content of each of which is incorporated herein by reference.

TECHNICAL FIELD

The present invention generally relates to an indwelling assembly and a method of using an indwelling assembly.

BACKGROUND DISCUSSION

In performing infusion into a patient or in other similar situations, an indwelling needle connected to an infusion line is made to puncture a patient's blood vessel and indwell in situ, so that the desired operation can be conducted.

An indwelling needle (indwelling needle assembly) includes a hollow outer needle used as a peripheral vein catheter, an outer needle hub firmly attached to the proximal end (base end) of the outer needle, an inner needle which is inserted in the outer needle and which has a sharp needlepoint at the distal end (tip) thereof, and an inner needle hub firmly attached to the proximal end of the inner needle. An example is disclosed in Japanese Patent Laid-open No. 2009-232916.

At the time of puncture of a patient's blood vessel by the indwelling needle, the puncturing operation is conducted in an assembled state wherein the inner needle is inserted in the outer needle and the needlepoint of the inner needle protrudes from the distal end of the outer needle.

When the needlepoint of the inner needle has reached the inside of the blood vessel, blood flowing in via an opening at the needlepoint passes through the lumen of the inner needle, and flows into the inside of the transparent inner needle hub (flashback). This helps enable the operator to confirm (visually confirm) that the inner needle has securely punctured the blood vessel.

After confirmation of the flashback, the outer needle is advanced, with the inner needle as a guide, and the outer needle is inserted into (made to puncture) the blood vessel.

Next, the inner needle is pulled out of the outer needle, a connector of the infusion line is connected to the outer needle hub, and an infusion liquid is dispensed.

Meanwhile, as a catheter which is longer than the above-mentioned peripheral vein catheter and is placed indwelling into a patient's blood vessel for dosing the patient with an infusion, for example, a central vein catheter, a PICC (Peripherally Inserted Central Catheter), a midline catheter and the like.

In order to put such a catheter indwelling in a patient's blood vessel, first, an introduction needle is made to puncture the patient's blood vessel. The puncture by the introduction needle is conducted by using the outer needle as the introduction needle. Then, the catheter is fed into the introduction needle, which places the catheter indwelling in the patient.

However, the procedure of indwelling the above-mentioned catheter in a blood vessel is relatively more complicated than the procedure of indwelling the above-mentioned outer needle in the blood vessel.

The lengths of the inner needle and the outer needle of the indwelling needle assembly can be selected to be large and to use the outer needle as the central vein catheter, PICC, or midline catheter.

When the lengths of the inner needle and the outer needle are selected to be relatively large, however, at the time of a puncturing operation, the inner needle and the outer needle may be deflected, making the puncturing relatively difficult. For example, where the inner needle is relatively thin and the inner needle and the outer needle are relatively easily deflected, it can be relatively difficult to achieve puncture.

SUMMARY

According to one aspect, an indwelling assembly comprises an inner needle having a sharp needlepoint at a distal end to puncture a blood vessel of a patient when the indwelling assembly is moved toward the patient, an inner needle hub fixed to the proximal portion of the inner needle, a hollow elongated outer member in which the inner needle is positioned, and an outer member hub fixed to the proximal portion of the hollow elongated outer member. The hollow elongated outer member is movable in the distal direction relative to the inner needle after puncturing the patient's blood vessel with the sharp needlepoint to position the hollow elongated outer member at a desired position in the blood vessel. A main body section is removably connected to the outer member hub so that the main body section is detachable from the outer member hub, and an elongated movable member is movable relative to the hollow elongated outer member and the outer member hub. The elongated movable member is connected to the inner needle hub so that the inner needle hub, the inner needle and the elongated movable member move together, with the elongated movable member projecting in the distal direction from the inner needle hub. A cover section covers an upper side of the elongated movable member, a part of the main body section is disposed under the cover section, and the outer member hub is disposed in an area between the elongate movable member and the cover section.

According to another aspect, an indwelling assembly comprises: an inner needle having a sharp needlepoint at a distal end to puncture a blood vessel of a patient when the indwelling assembly is moved toward the patient, an inner needle hub fixed to the proximal portion of the inner needle so that the inner needle and the inner needle hub move together as unit, a hollow elongated outer member in which the inner needle is positioned, and an outer member hub fixed to the proximal portion of the hollow elongated outer member so that the hollow elongated outer member and the outer member hub move together as unit. The hollow elongated outer member is movable in the distal direction relative to the inner needle after puncturing the patient's blood vessel with the sharp needlepoint to position the hollow elongated outer member at a desired position in the blood vessel. An elongated movable member is connected to the outer member hub so that the elongated movable member, the outer member hub and the hollow elongated outer member move together. The elongated movable member includes two spaced apart side portions projecting upwardly away from a bottom portion so that the two side portions and the bottom portion together define a space. The elongated movable member projects in the distal direction from the inner needle hub, and the inner needle is positioned in the space before puncturing the patient's blood vessel. A main body section is connected to the outer member hub so that the main body section and the outer member hub move together. The main body section is also detachable from the outer member hub, and a part of the main body section overlies the outer member hub. A cover section overlies a part of the space in the elongated movable member and also overlies a part of the main body section positioned in the space so that the part of the main body section is positioned between the bottom portion of the elongated movable member and the cover section. A portion of the main body section is uncovered by the cover section before puncturing the patient's blood vessel so that the portion of the main body section is engageable by a user's finger to move the hollow elongated outer member in the distal direction relative to the inner needle after puncturing the patient's blood vessel to thereby position a distal end of the hollow elongated outer member distally beyond the sharp needlepoint.

DETAILED DESCRIPTION

Set forth below, with reference to the accompanying drawings, is a detailed description of several embodiments of an indwelling needle assembly and method of use representing examples of the indwelling needle assembly and method disclosed here.

In the following example, description will be made by referring to the left side in FIGS. 1 to 5 as the "proximal (end)" or rear end, the right side as the "distal (end)" or front end, the upper side as the "upper" and the lower side as the "lower."

Figure 1:
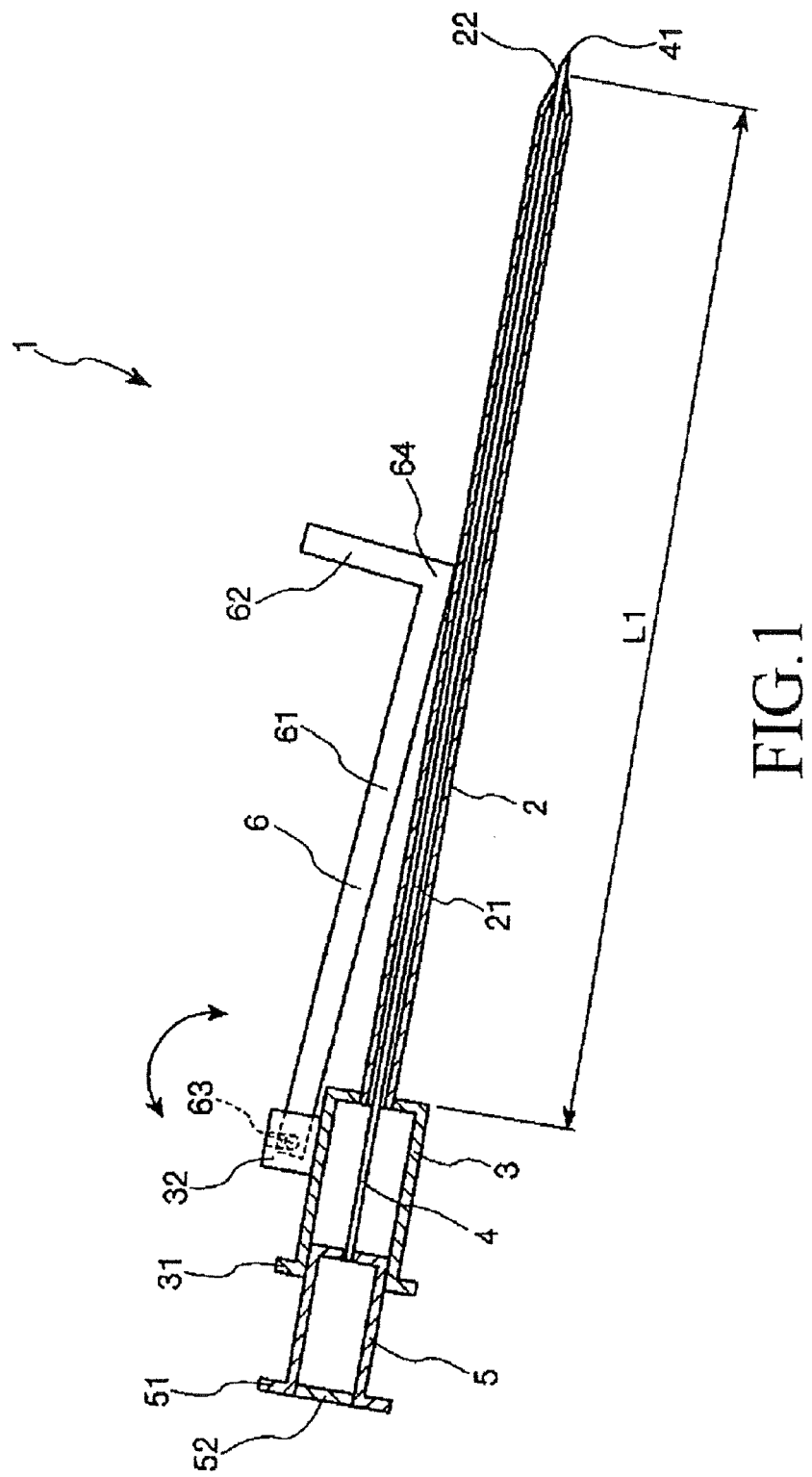
FIG. 1 is a cross-sectional view showing a first embodiment of an indwelling needle assembly.

As shown in FIG. 1, the indwelling needle assembly 1 includes a hollow outer needle 2, an outer needle hub 3 fixed to a proximal portion of the outer needle 2, an inner needle 4 inserted in the outer needle 2, an inner needle hub 5 fixed to a proximal portion of the inner needle 4, and a pressing member 6 connected to the outer needle hub 3.

By way of example, the outer needle 2 has a certain degree of flexibility. For example, the material constituting the outer needle 2 is a resin material, such as a flexible resin material. Examples of the resin material include fluoro-resins such as PTFE, ETFE, PFA, etc., olefin reins such as polyethylene, polypropylene, etc. or mixtures thereof, poly-urethane, polyesters, polyamides, polyether-nylon resins, mixtures of the olefin resin with an ethylene-vinyl acetate copolymer, and the like.

An outer needle 2 as disclosed may have inside visibility at the whole part or a part thereof. Besides, the material forming the outer needle 2 may be admixed with a radiopaque material, e.g., barium sulfate, barium carbonate, bismuth carbonate, or tungstic acid, whereby a radiopaque contrast function can be imparted to the material.

In addition, the length L1 of the outer needle 2 is not limited and can be set appropriately according to the use or various conditions. By way of example, the length L1 of the outer needle 2 can be set in the range of about 2.0 to 50.0 cm, for example, about 3.0 to 40.0 cm, and for example, about 10.0 to 30.0 cm.

The length L1 of the outer needle 2 helps ensure that the outer needle 2 can be used as a catheter which is longer than peripheral vein catheters, such as, for example, a central vein catheter, a PICC, or a midline catheter. Incidentally, the outer needle 2 may naturally be used as a peripheral vein catheter.

To a proximal portion of the outer needle 2, the outer needle hub 3 is attachable, for example, firmly attached or fixed, in a liquid-tight manner by such a method as caulking, welding (heat welding, microwave welding, etc.), or adhesion with an adhesive.

The outer needle hub 3 is composed of a substantially tubular member, and the inside thereof communicates with a lumen 21 of the outer needle 2. Besides, the outer needle hub 3 is formed with a flange 31 at an outer circumferential part of a proximal portion of the outer needle hub 3.

Figure 2:
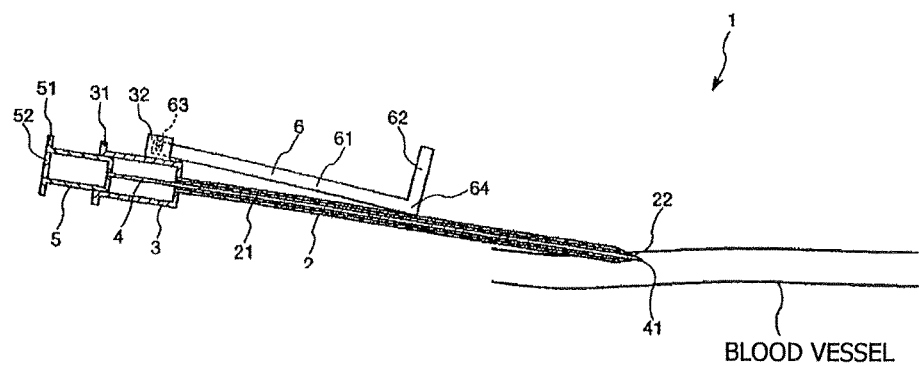
FIG. 2 is a cross-sectional view illustrating an example of a method of using the indwelling needle assembly shown in FIG. 1.

In the outer needle 2 is inserted the inner needle 4 which has a sharp needlepoint 41 at its distal end. The indwelling needle assembly 1 is used in the state in which the inner needle 4 is inserted in the outer needle 2 and an inner needle hub 5 to be disclosed later is fitted to the outer needle hub 3 (the state in which the needlepoint 41 protrudes from a distal opening 22 of the outer needle 2), namely, in the state as shown in FIGS. 1 and 2. By way of example, this state will be referred to as "the assembled state"

The length of the inner needle 4 is so set that, in the assembled state, at least the needlepoint 41 protrudes from the distal opening 22 of the outer needle 2.

The inner needle 4 may be a hollow needle, and may also be a solid needle. Where the inner needle 4 is a solid needle, relatively sufficient strength can be secured while setting the outside diameter of the inner needle 4 small. In addition, where the inner needle 4 is a solid needle, the solid needle helps ensure that in discarding the inner needle 4 after an operation is finished, such a risk as remaining of blood inside the inner needle 4 or flowing-out of the remaining blood is relatively absent, so that relatively high safety is secured.

By way of example, where the inner needle 4 is a hollow needle, upon puncture of a blood vessel by the inner needle 4 blood flows into the hollow part of the inner needle 4 and the flashback of the blood is confirmed by the user. In this connection, where the inner needle 4 is a solid needle, blood flows into the gap between the inner needle 4 and the outer needle 2, so that the flashback of the blood can be confirmed more swiftly.

For example, while the inner needle 4 may have a configuration in which it has both a hollow part and a solid part (e.g., a configuration in which the lumen of a hollow needle is partly filled so that the needle is hollow on the distal side and solid on the proximal side), a configuration in which the whole body of the inner needle 4 is composed of a single member helps reduce the cost of the inner needle 4.

In addition, the inner needle 4 may be constant in outside diameter, or may have plural (in this embodiment, three) parts which are different in outside diameter.

Examples of the material constituting such an inner needle 4 as above-mentioned include metallic materials such as stainless steel, aluminum or aluminum alloys, and titanium or titanium alloys.

By way of example, the inner needle 4 is such that when its part corresponding to a pressing section 64 of the pressing member 6 to be disclosed later (its part to be pressed by the pressing section 64) is fixed and a force of about 0.1 N in a direction perpendicular to the axis of the inner needle 4 is exerted on its distal portion, the displacement of the distal portion in the direction perpendicular to the axis of the inner needle 4 will be not more than about 3.0 mm, for example not more than about 2.0 mm.

The inner needle hub 5 can be fixed to a proximal portion of the inner needle 4.

The inner needle hub 5 is composed of a substantially tubular member, and a flange 51 is formed at an outer circumferential part of a proximal portion thereof. In the assembled state, that part of the inner needle hub 5 which is on the distal side relative to the flange 51 is inserted in the inside of the outer needle hub 3, and is fitted and fixed there.

For example, at a proximal-side opening of the inner needle hub 5, a vent filter 52 is disposed so as to cover the opening. The vent filter 52 has such a property as to permit gas to pass therethrough, and block the passage of liquid therethrough.

Examples of the vent filter 52 include various sintered porous bodies, hydrophobic non-woven fabrics, and other porous bodies. For example, the sintered porous bodies are those obtained by sintering a material containing a polymer material (powder) such as polyethylene and a hydrophilic (water-soluble, or water-swellable) polymer. When the sintered porous body is used, its contact with liquid (blood) blocks ventilation as well, which helps prevent the external intrusion of air. For example, where the inner needle 4 is a solid needle, it is unnecessary to provide the vent filter 52.

Examples of the method for fixing the inner needle 4 to the inner needle hub 5 include such method as fitting, caulking, welding, or adhesion with an adhesive, and combinations of these methods.

By way of example, an inner needle hub 5 and the above-disclosed mentioned outer needle hub 3 can be formed respectively from transparent (colorless transparent), colored transparent or semi-transparent resins, whereby visibility of the inside thereof is secured. This helps ensure that when the outer needle 2 has securely reached the inside of a blood vessel, the flashback of blood flowing in can be confirmed by visual observation.

Materials constituting the outer needle hub 3 and the inner needle hub 5 are not restricted. Examples of the materials include various resin materials such as polyolefins such as polyethylene, polypropylene, ethylene-vinyl acetate copolymer, etc., polyurethane, polyamides, polyesters, polycarbonate, polybutadiene, polyvinyl chloride, and polyacetal.

The pressing member 6 has the pressing section 64 which is pressed by a finger against that part (intermediate part) of the outer needle 2 between the proximal end and the distal end of the outer needle 2, at the time of a puncturing operation of causing the needlepoint 41 of the inner needle 4 and a distal portion of the outer needle 2 in the assembled state to puncture a blood vessel, in a process for setting the outer needle 2 indwelling in the blood vessel. By the pressing section 64, that part of the outer needle 2 between the proximal end and the distal end is pressed.

For example, the pressing member 6 includes an elongate main body section 61 disposed along the axis (center axis) of the outer needle 2 and located on the outer needle 2, a finger hook projection 62 which is provided in the main body section 61 and on which a finger is placed, and the pressing section 64 composed of that part of the main body section 61 which is on the opposite side in the vertical direction from the finger hook projection 62. The finger hook projection 62 is formed at a distal portion of the main body section 61 so as to project upward. Those parts of the finger hook projection 62 and the main body section 61 which are to be contacted by a finger are, for example, flat surfaces, or curved recessed surfaces, or curved protuberant surfaces. An upper-side part of the pressing member 6 constitutes a finger contact section on which a finger is placed.

By way of example, while the pressing section 64 is provided by utilizing the distal portion of the main body section 61 of the present embodiment. For example, the pressing section 64 may be composed of a projection formed at that part of the main body section 61 which is on the opposite side in the vertical direction from the finger hook projection 62.

In addition, a proximal portion of the pressing member 6, or a proximal portion of the main body section 61, is connected to the outer needle hub 3. This structure helps enable the finger hook projection 62 to serve also as a part to be pressed by a finger at the time of moving the outer needle 2 in the distal direction relative to the inner needle 4, in the process of putting the outer needle 2 indwelling in a blood vessel. For example, the pressing member 6 naturally may be connected to other member, such as the inner needle hub 5.

The pressing member 6 can be connected to the outer needle hub 3 in such a manner as to be turnable (displaceable) relative to the outer needle hub 3. For example, a hinge structure section is composed of a shaft 63 provided at a proximal portion of the main body section 61, and a bearing 32 provided on the upper portion of the outer surface of the outer needle hub 3 for supporting the shaft 63, and, owing to the hinge structure section, the pressing member 6 can be turned relative to the outer needle hub 3, with the proximal portion of the main body section 61 as a center of turning.

Figure 5A:
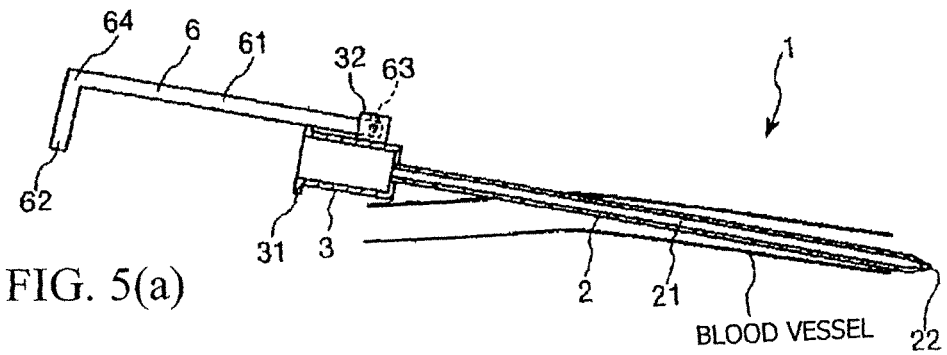
FIGS. 5a-5c are cross-sectional views illustrating an example of a method of using the indwelling needle assembly shown in FIG. 1.

In addition, the pressing member 6 is configured to be displaceable into a first position shown in FIG. 1 where it is disposed along the axis of the outer needle 2 and a second position shown in FIG. 5(a) where it is retracted from the outer needle 2.

When the pressing member 6 is situated in the first position, the pressing member 6 is located on the outer needle 2. In addition, the distal portion of the pressing member 6, or the finger hook projection 62 and the pressing section 64 are located on the distal side relative to the proximal portion of the outer needle 2 and on the proximal side relative to the distal portion of the outer needle 2. This configuration helps ensure that even in the case where the inner needle 4 and the outer needle 2 are comparatively large in length, at the time of a puncturing operation, by pressing down that part of the outer needle 2 between the proximal end and the distal end (that part of the outer needle 2 corresponding to the pressing section 64 of the pressing member 6) through the pressing section 64, to restrain the inner needle 4 and the outer needle 2 from deflection and to carry out the puncturing operation relatively easily and assuredly.

By way of example, since the puncturing operation can be performed by putting the finger on the finger hook projection 62 of the pressing member 6 that is located nearer to the distal portions of the inner needle 4 and the outer needle 2 than the inner needle hub 5 and the outer needle hub 3, the needlepoint 41 of the inner needle 4 can be controlled relatively easily during the puncturing operation.

In addition, when the pressing member 6 is situated in the second position, the pressing member 6 is located on the proximal side relative to the outer needle 2. The pressing member 6 can be moved into this second position, in the case where the pressing member 6 would otherwise be an obstacle to the operator (user) or the patient (the person for which the assembly is used) during the process of putting the outer needle 2 indwelling in a blood vessel or after the outer needle 2 is put indwelling in the blood vessel or in other similar situation.

For example, the pressing member 6 is configured to be attachable to and detachable from the outer needle hub 3. The shaft 63 is provided at a proximal portion of the main body section 61 and can be detachably attached to the bearing 32 provided in the outer needle hub 3. This configuration helps enable the pressing member 6 to be detached in the case where the pressing member 6 would otherwise be an obstacle to the operator or the patient during the process of putting the outer needle 2 indwelling in a blood vessel or after the outer needle 2 is put indwelling in the blood vessel or in other similar situation. In addition, when the pressing member 6 becomes necessary, the pressing member 6 can be attached.

By way of example, the dimensions of the pressing member 6 are not limited, insofar as that part of the outer needle 2 between the proximal end and the distal end can be pressed by the pressing section 64 of the pressing member 6.

In addition, the pressing member 6 can be sized that when the pressing member 6 is pressed by a finger, the finger does not touch the outer needle 2, which enhances safety. For example, the outer needle 2 as well as the parts to be brought into contact with the outer needle 2, such as a back surface of the pressing member 6, is in a sterilized state.

The material constituting the pressing member 6 is not restricted, and for example, the same or similar materials to those mentioned as examples of the materials for forming the outer needle hub 3 and the inner needle hub 5 above can be used.

According to an aspect, a method of using the indwelling needle assembly 1 (in the case of puncturing a blood vessel) (operation) is disclosed below.

As shown in FIG. 2, the indwelling needle assembly 1 is put into the assembled state, and the pressing member 6 is positioned in the first position. The inner needle hub 5 is gripped by one hand, and an index finger is put on the finger hook projection 62 of the pressing member 6. While pressing down the vicinity of a base part of the finger hook projection 62 by the index finger, a distal portion of the indwelling needle assembly 1 (the united distal portion of the outer needle 2 and the inner needle 4) is made to puncture a skin of a patient toward a blood vessel, in the manner of pressing the united distal portion against the patient. In this instance, as above-mentioned, the pressing section 64 presses down that part of the outer needle 2 between the proximal end and the distal end, whereby the inner needle 4 and the outer needle 2 can be restrained from deflection. Incidentally, the inner needle hub 5 naturally may be gripped by the left hand.

When the needlepoint 41 of the inner needle 4 has punctured the blood vessel, the blood pressure causes blood to flow back in the proximal direction through the inner needle 4, to be introduced into the inner needle hub 5, and this flashback can be visually confirmed through the inner needle hub 5 having visibility. As a result, one can know that the needlepoint 41 of the inner needle 4 has relatively securely punctured the blood vessel.

Incidentally, attendant on the inflow of the blood, air in the inner needle hub 5 is discharged via the vent filter 52. However, since the blood does not pass through the vent filter 52, this helps ensure that the blood does not leak to the exterior.

Figure 3:
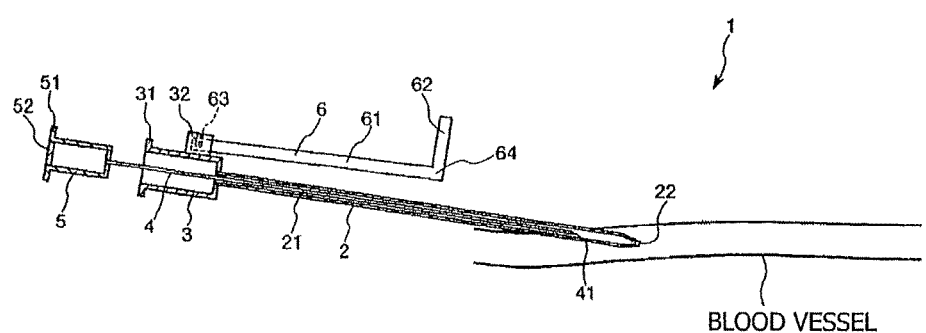
FIG. 3 is a cross-sectional view illustrating an example of a method of using the indwelling needle assembly shown in FIG. 1.

As shown in FIG. 3, the outer needle 2 is advanced further by a minute distance in the distal direction along the inner needle 4, with the inner needle 4 as a guide. For example, the finger hook projection 62 is pushed in the distal direction by the index finger, to move the outer needle 2 in the distal direction.

Figure 4:
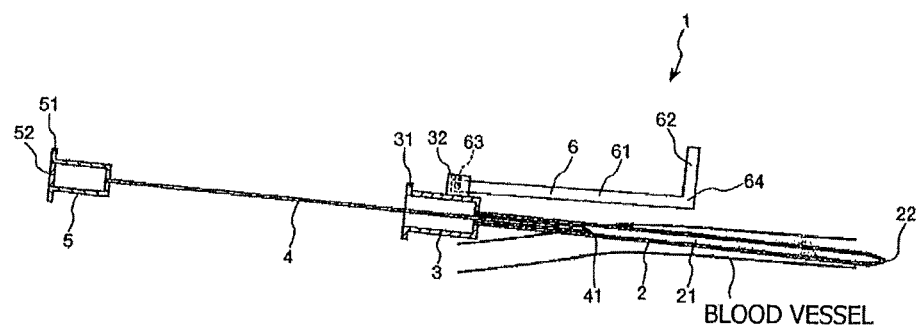
FIG. 4 is a cross-sectional view illustrating an example of a method of using the indwelling needle assembly shown in FIG. 1.

Subsequently, as shown in FIG. 4, while fixing the position of the inner needle hub 5 with the other hand, the outer needle hub 3 is gripped, and the outer needle 2 is advanced further in the distal direction along the inner needle 4, with the inner needle 4 as a guide. In this manner, a distal portion of the outer needle 2 is inserted to a target position in the blood vessel.

Figure 5B:
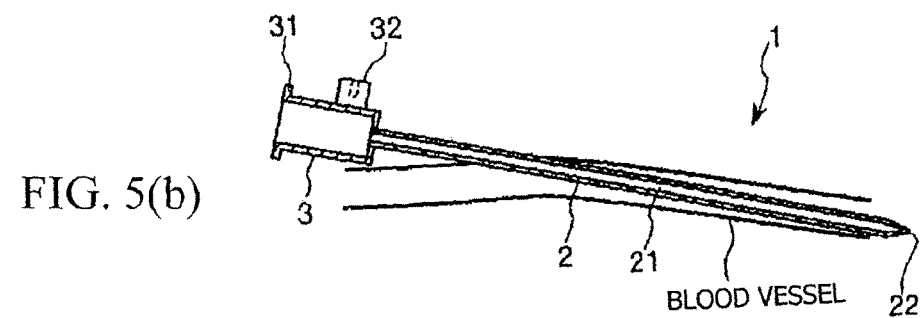
Figure 5C:
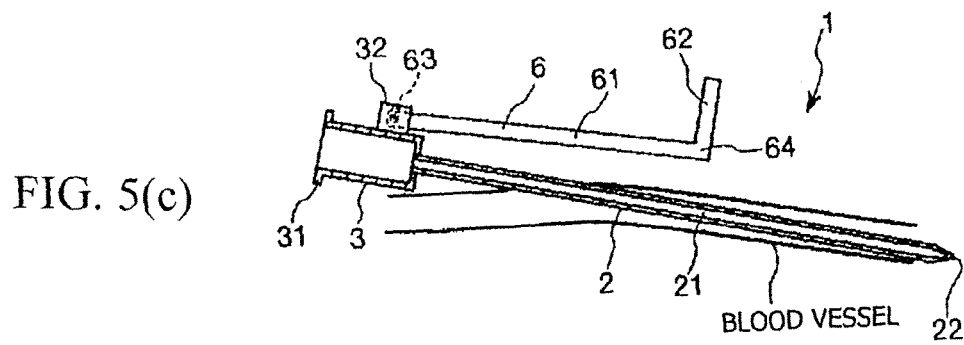

Next, while holding down by the left hand the outer needle hub 3 and the pressing member 6 on the side of the outer needle 2 kept indwelling in the blood vessel, the inner needle hub 5 is gripped by the right hand and is pulled in the proximal direction. This results in that the inner needle 4 is pulled out of the outer needle 2. After the inner needle 4 is thus pulled out of the outer needle 2, if necessary, as shown in FIG. 5(*a*), the pressing member 6 may be positioned into the second position by turning. Alternatively, as shown in FIG. 5(*b*), the pressing member 6 may be detached from the outer needle hub 3. Further, as shown in FIG. 5(*c*), the pressing member 6 may be left as it is.

To the outer needle hub 3 from which the inner needle 4 has been pulled out, a connector of an infusion set (not shown) is relatively quickly connected, and dispensing of an infusion liquid is started following the normal procedure.

After the inner needle 4 is pulled out of the outer needle 2 in accordance with this embodiment, the inner needle 4 and the inner needle hub 5 are unnecessary and can be disposed of.

As disclosed above, according to the indwelling needle assembly 1, in the embodiment where the inner needle 4 and the outer needle 2 are comparatively large in length, by pressing down that part of the outer needle 2 between the proximal end and the distal end through the pressing section 64 of the pressing member 6 at the time of a puncturing operation, to relatively restrain the inner needle 4 and the outer needle 2 from deflection and to carry out the puncturing operation relatively easily and assuredly.

In addition, since the puncturing operation can be conducted by putting a finger on the finger hook projection 62 of the pressing member 6 that is nearer to the distal portions of the inner needle 4 and the outer needle 2 than the inner needle hub 5 and the outer needle hub 3, the needlepoint 41 of the inner needle 4 can be controlled during the puncturing operation relatively easily.

By way of example, by putting a finger on the finger hook projection 62 and pushing the finger hook projection 62 in the distal direction, the outer needle 2 can be moved in the distal direction relative to the inner needle 4 relatively easily and assuredly.

In the following exemplary embodiment, description will be made by referring to the left side in FIGS. 6 to 11 as "distal (end)," the right side as "proximal (end) (rear end)," the upper side as "upper" and the lower side as "lower." In addition, in FIGS. 6 to 11, a blood vessel is omitted from drawing.

According to a second embodiment will be disclosed below referring mainly to differences from the above-disclosed first embodiment, and descriptions of the same items as above will be omitted.

Figure 6:
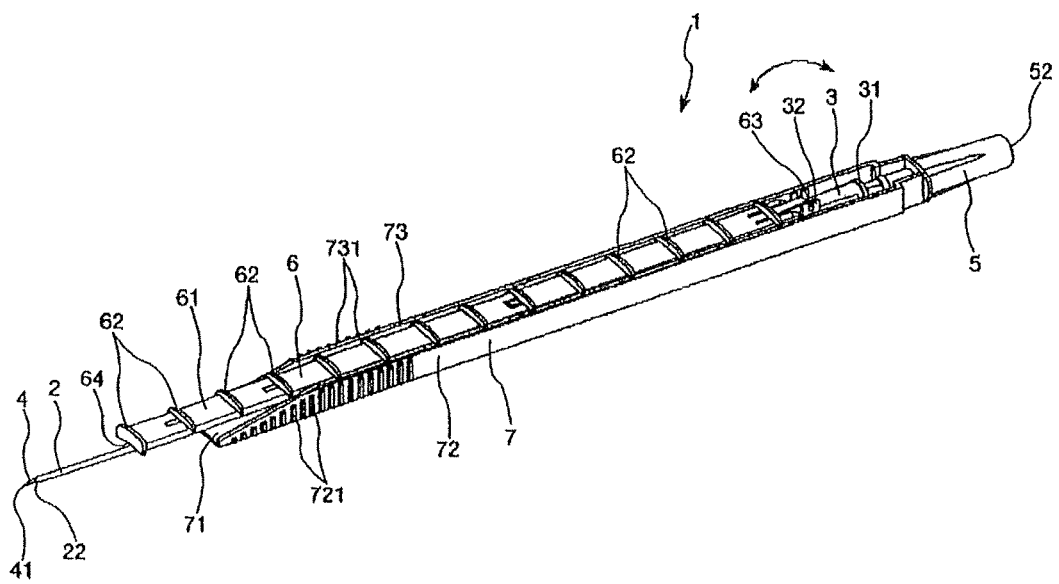
FIG. 6 is a perspective view of a second embodiment (assembled state) of an indwelling needle assembly.
Figure 7:
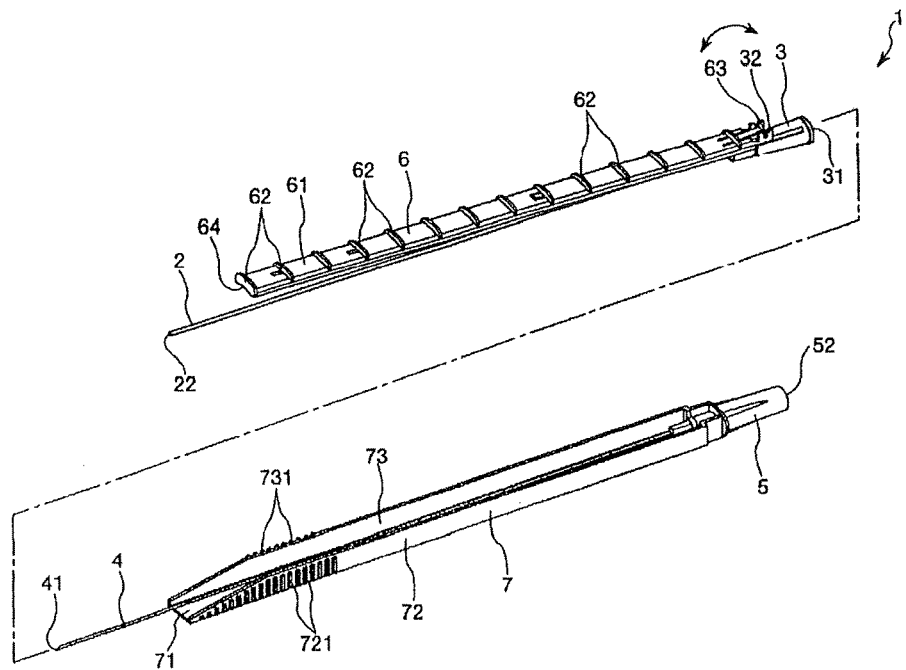
FIG. 7 is a perspective view of the second embodiment (non-assembled state) of the indwelling needle assembly.

As shown in FIGS. 6 and 7, in the indwelling needle assembly 1 according to the second embodiment, a plurality of finger hook projections 62 of a pressing member 6 are provided in a main body section 61 along the axis of an outer needle 2. By way of example, in the configuration shown, the finger hook projections 62 are disposed at regular intervals. The finger hook projections 62 have the function as graduations indicative of the length of insertion of the outer needle 2 into a blood vessel, in addition to the function described in the first embodiment.

In addition, a pressing section 64 in this embodiment is composed of that part of the main body section 61 which is located on the opposite side in the vertical direction from the finger hook projection 62 at the distal-most end.

By way of example, those parts of the main body section 61 which are located on the opposite side in the vertical direction from the finger hook projections 62 may constitute pressing sections, respectively. For example, a predetermined part of a plurality of parts of the outer needle 2 between the proximal end and the distal end can be selectively pressed.

The indwelling needle assembly 1 has a grip member 7 which has a proximal portion connected (fixed) to an inner needle hub 5 and which protrudes from the inner needle hub 5 in the distal direction. This helps ensure that at the time of an operation of putting the outer needle 2 indwelling in a blood vessel, the grip member 7 can be gripped by hand and the operation can be carried out relatively easily and assuredly.

The grip member 7 is elongated in shape, and is composed of a bottom plate 71 and two wall sections 72 and 73 rising up from the bottom plate 71. An inner needle 4 is disposed in a space on the inside of the grip member 7.

In addition, in the assembled state, the pressing member 6 is contained in the space on the inside of the grip member 7 so as to be movable in the longitudinal direction thereof. The grip member 7 has a function as a guide member which, when the pressing member 6 is moved in the distal direction, relatively restricts the moving direction of the pressing member 6. This helps ensures that when the pressing member 6 is moved in the distal direction, the pressing member 6 can be prevented from coming out of position in the transverse direction.

By way of example, at outside surfaces of distal portions of the side walls 72 and 73, a plurality of ribs 721 and 731 extending in the vertical direction are respectively arrayed as hand slip preventive means. This helps ensures that when the grip member 7 is gripped with a hand, the hand can be prevented from slipping.

As shown in FIG. 6, in the assembled state, the pressing member 6 is stored in the space on the inside of the grip member 7.

In addition, in the assembled state, a distal portion of the grip member 7 is located on the distal side relative to a proximal portion of the outer needle 2, and is located on the proximal side relative to a distal portion of the inner needle 4.

By way of example, in the assembled state, when the pressing member 6 is positioned in the first position, the distal portion of the grip member 7 is located on the proximal side relative to the distal portion of the pressing member 6.

This helps ensure that a puncturing operation and an operation of moving the outer needle 2 in the distal direction relative to the inner needle 4 can be carried out easily and assuredly.

By way of example, the material constituting the grip member 7 is not restricted. For example, the same or similar materials as those mentioned as examples of the materials for forming the outer needle hub 3 and the inner needle hub 5 above can be used.

An example of the method of using the indwelling needle assembly 1 (in the case of puncturing a blood vessel) (operation) will be described below.

As shown in FIG. 6, the indwelling needle assembly 1 is put into the assembled state, and the pressing member 6 is positioned in the first position. Then, a distal portion of the grip member 7 provided at the inner needle hub 5 is gripped with the right hand (one hand), and an index finger of the right hand is put on the distal-most finger hook projection 62 of the pressing member 6. While pressing down the vicinity of a base portion of the finger hook projection 62 by the index finger, a distal portion of the indwelling needle assembly 1 is made to puncture a skin of a patient toward a blood vessel, in such a manner as to press the distal portion against the patient. By way of example, the pressing section 64 presses down that portion of the outer needle 2 between the proximal end and the distal end, whereby the inner needle 4 and the outer needle 2 can be restrained from deflection.

When a needlepoint 41 of the inner needle 4 has punctured a blood vessel, the internal pressure of the blood vessel causes blood to flow back in the proximal direction through the inner needle 4, to be introduced into the inner needle hub 5, so that this flashback can be visually confirmed through the inner needle hub 5 having visibility. As a result, it can be known that the needlepoint 41 of the inner needle 4 has relatively securely punctured the blood vessel.

Figure 8:
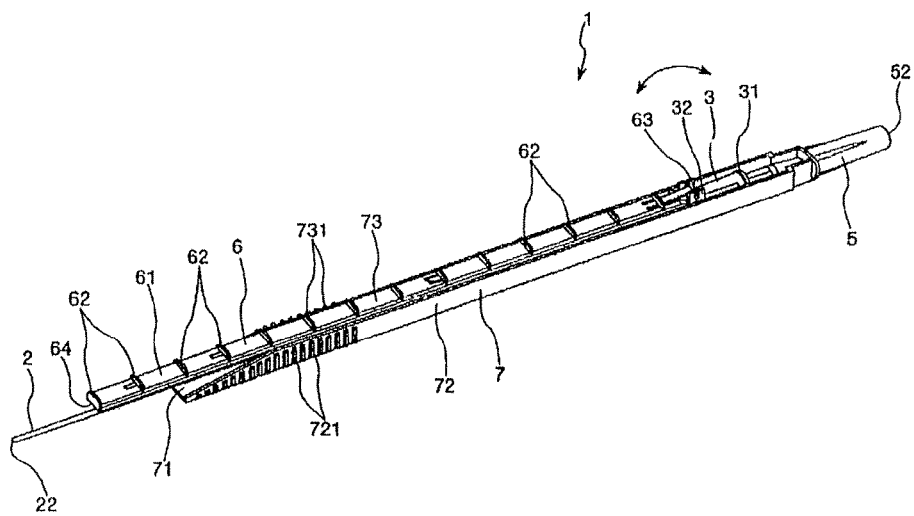
FIG. 8 is a perspective view illustrating an example of a method of using the indwelling needle assembly shown in FIG. 6.

Next, as shown in FIG. 8, the outer needle 2 is further advanced by a minute distance in the distal direction along the inner needle 4, with the inner needle 4 as a guide. By way of example, the distal-most finger hook projection 62 is pushed in the distal direction by the index finger, to move the outer needle 2 in the distal direction.

Figure 9:
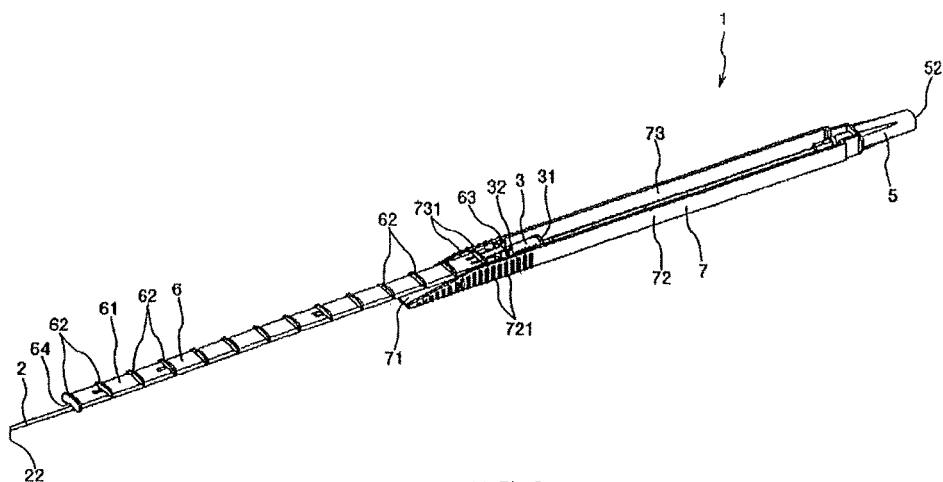
FIG. 9 is a perspective view illustrating an example of a method of using the indwelling needle assembly shown in FIG. 6.

Subsequently, as shown in FIG. 9, the second distal-most finger hook projection 62 is pushed in the distal direction by the index finger, to move the outer needle 2 by a minute distance in the distal direction, and such an operation is sequentially repeated to insert a distal portion of the outer needle 2 to a target position in the blood vessel.

Figure 10:
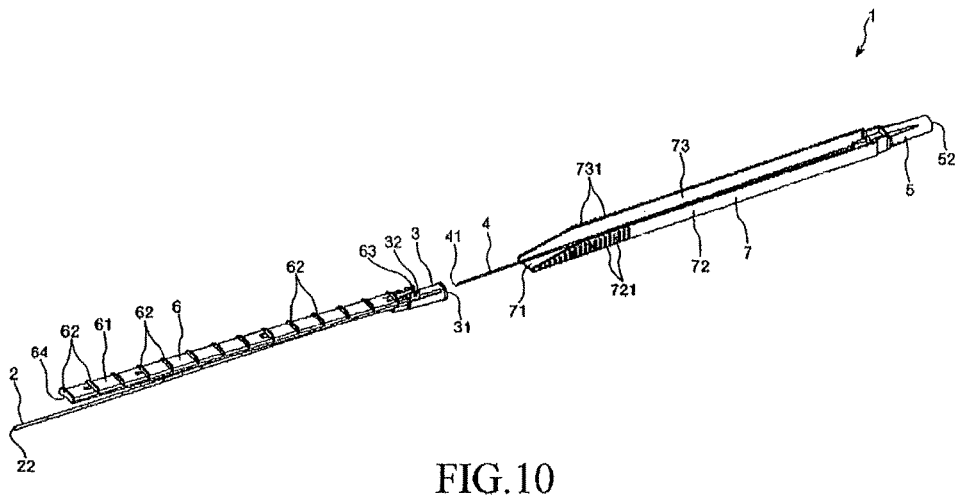
FIG. 10 is a perspective view illustrating an example of a method of using the indwelling needle assembly shown in FIG. 6.
Figure 11:
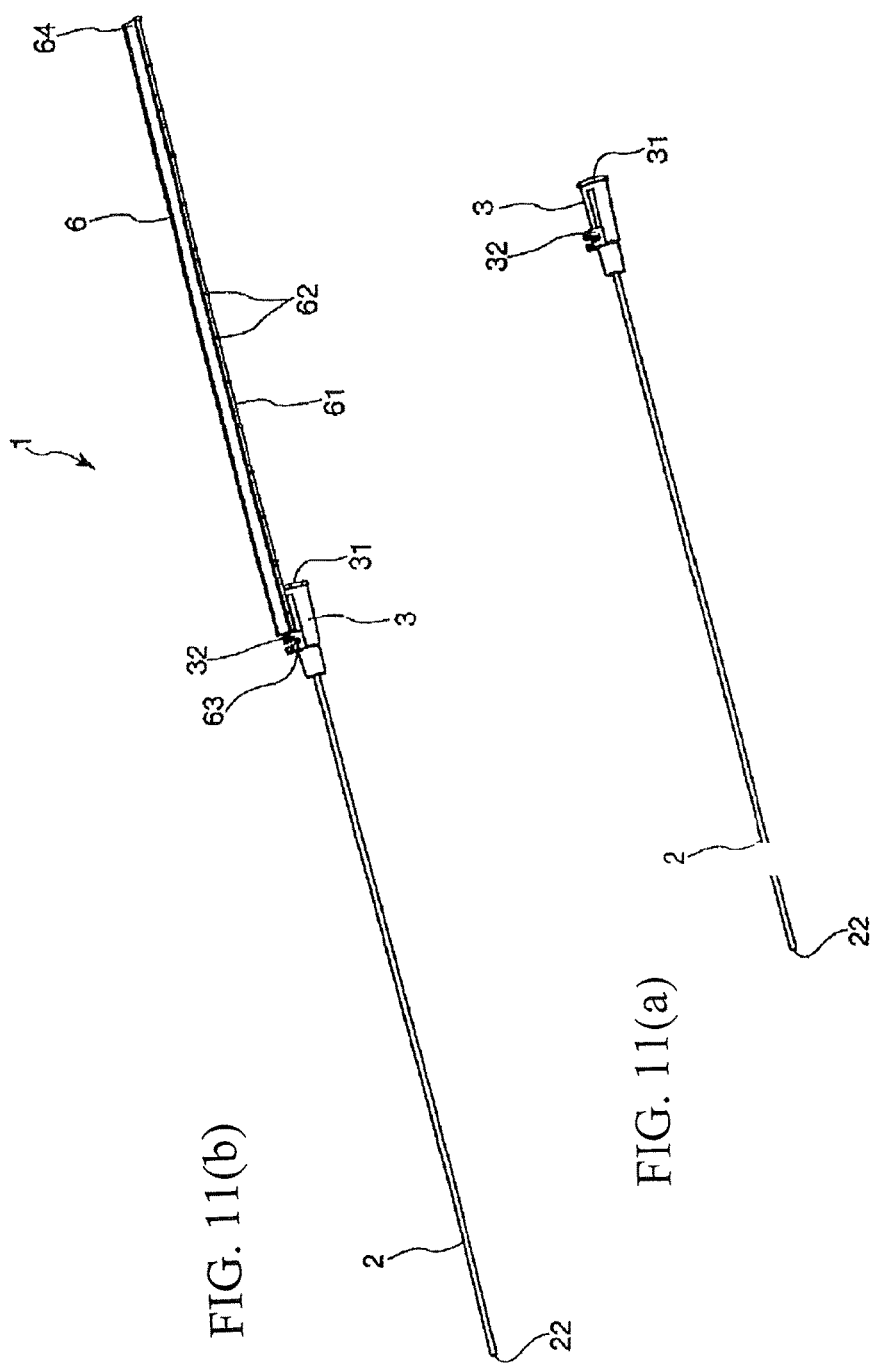
FIGS. 11a and 11b are perspective views illustrating an example of a method of using the indwelling needle assembly shown in FIG. 6.

Next, as shown in FIG. 10, while holding down by the left hand the pressing member 6 on the side of the outer needle 2 kept indwelling in the blood vessel, a proximal portion of the grip member 7 and the inner needle hub 5 are gripped by the right hand and pulled in the proximal direction. As a result, the inner needle 4 is pulled out of the outer needle 2. After the inner needle 4 is pulled out of the outer needle 2, if necessary, as shown in FIG. 11(*a*), the pressing member 6 may be detached from the outer needle hub 3. Alternatively, as shown in FIG. 11(*b*), the pressing member may be positioned into the second position by turning. Further, the pressing member 6 may be kept as it is. By way of example, the subsequent operations are the same as in the first embodiment, and, therefore, descriptions of the subsequent operations are omitted.

According to this indwelling needle assembly 1, the same effects as those of the above-described first embodiment can be obtained.

For example, since the plurality of finger hook projections 62 are provided along the axis of the outer needle 2 in this indwelling needle assembly 1, by sequentially pushing the finger hook projections 62 in the distal direction, to move the outer needle 2 in the distal direction relative to the inner needle 4 relatively easily and assuredly.

In addition, since the grip member 7 is provided, the operation of putting the outer needle 2 indwelling in a blood vessel can be carried out relatively easily and assuredly.

In the following example, description will be made by referring to the left side in FIGS. 12 to 14 and FIGS. 16 to 22 as "distal (end)," the right side as "proximal (end) (rear end)," the upper side as "upper" and the lower side as "lower." In addition, in FIGS. 18 to 22, a blood vessel is omitted from drawing.

A third embodiment will be disclosed below referring mainly to differences from the above-described second embodiment, and descriptions of the same items as above will be omitted.

As shown in FIGS. 12, 13, 19 and 20, in the indwelling needle assembly 1 according to the third embodiment, the pressing member 6 is configured to be curved or bent in a direction for coming away from the outer needle 2, at an intermediate portion in the longitudinal direction thereof. For example, a small material thickness section 611 is formed at an intermediate portion in the longitudinal direction of a main body section 61 of the pressing member 6, and the pressing member 6 is curved or bent through bending deformation of the small material thickness section 611. In addition, the small material thickness section 611 is formed at a plurality of locations (in the configuration shown, two locations) along the longitudinal direction of the main body section 61. Incidentally, the number of the location(s) at which the small material thickness section 611 is formed may naturally be one.

By way of example, this helps ensure that at the time of moving the outer needle 2 in the distal direction in putting the outer needle 2 indwelling in a blood vessel, it is relatively ensured that even if the distal portion of the pressing member 6 abuts on a predetermined part of the patient, the pressing member 6 is curved or bent at its intermediate portion, whereby interference between the pressing member 6 and the patient's predetermined part can be avoided. As a result, the outer needle 2 can be moved relatively easily and smoothly. For example, in the case of puncturing a patient's skin from the inside of an upper arm part and inserting the distal end of the outer needle 2 to a position immediately on the operator's side of the patient's side part, a gradual movement of the pressing member 6 in the distal direction may cause a distal portion of the pressing member 6 to abut on a knot of muscle corresponding to the biceps muscle of arm. By way of example, in such a situation, the pressing member 6 would not be an obstacle, since it is curved or bent at its intermediate portion.

In addition, the layout of the two small material thickness sections 611 is not limited. By way of example, in this embodiment, a setting of L1<L2 is adopted, where L1 (see FIG. 21) is the length in the longitudinal direction between the distal end of the pressing member 6 and the small material thickness section 611 on the distal side, and L2 (see FIG. 21) is the length in the longitudinal direction between the small material thickness section 611 on the distal side and the small material thickness section 611 on the proximal side.

The lengths L1 and L2 are not restricted, respectively, and may be appropriately set according to various conditions. By way of example, the length L1 can be about 10 to 30 mm, for example, about 15 to 20 mm. In addition, the length L2 can be about 20 to 90 mm, for example about 30 to 70 mm.

Figure 14:
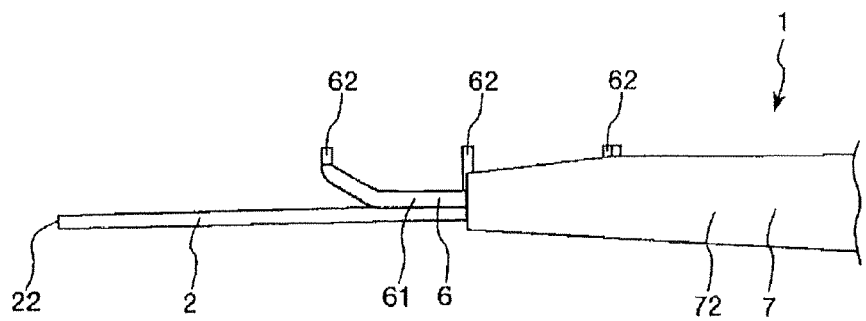
FIG. 14 is a side view of the pressing member and an outer needle of the indwelling needle assembly shown in FIG. 12.

As shown in FIG. 14, a distal portion of the pressing member 6 is so provided as to be directed upward (in such a direction as to come away from the outer needle 2 in a radial direction of the outer needle 2). For example, the distal portion of the pressing member 6 can be warped so as to come away from the outer needle 2, which helps ensure that in the case of moving the outer needle 2 in the distal direction in putting the outer needle 2 indwelling in a blood vessel. In addition, it also helps ensure that even if the distal portion of the pressing member 6 comes into contact with on a predetermined part of the patient, the distal portion of the pressing member 6 can ride over the predetermined part relatively easily and smoothly, whereby the outer needle 2 can be moved.

Figure 15:
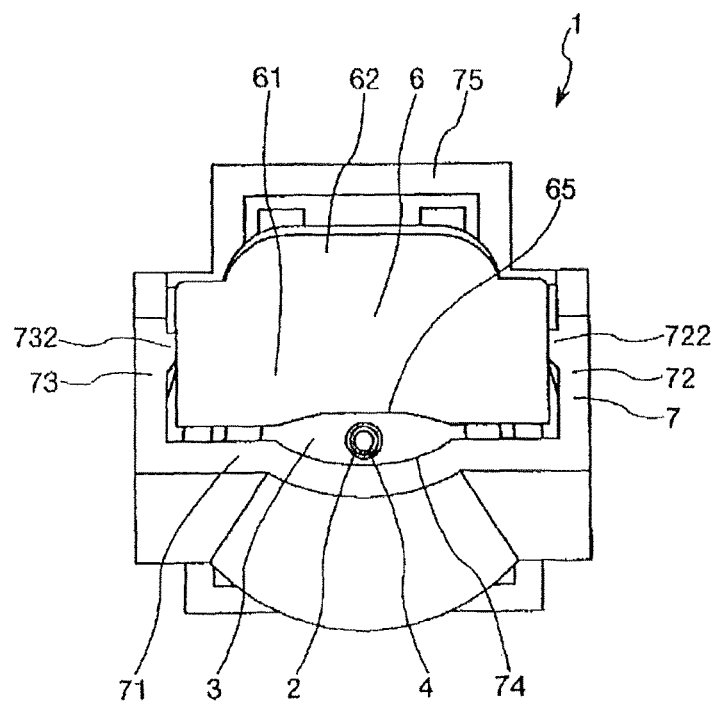
FIG. 15 is a front view of the indwelling needle assembly shown in FIG. 12.

As shown in FIG. 15, the indwelling needle assembly 1 has a groove (recess) 65 formed in the pressing member 6, and a groove (recess) 74 formed in a grip member 7, as slip-off preventive means for helping prevent the outer needle 2 from coming out of position in a direction perpendicular to the axis of the outer needle 2, for example, in a transverse direction in FIG. 15.

The groove 65 is formed in a lower surface of the main body section 61 of the pressing member 6, and extends along the longitudinal direction of the pressing member 6. By way of example, while the groove 65 is formed over the whole length, from the distal end to the proximal end, of the main body section 61 in the configuration shown, this configuration is not restrictive. For example, the groove 65 may be formed only in a distal portion of the main body section 61.

In addition, the groove 74 is formed in an upper surface of a bottom plate 71 of the grip member 7 at a position corresponding to the groove 65, and extends along the longitudinal direction of the grip member 7. For example, while the groove 74 is formed over the whole length, from the distal end to the proximal end, of the bottom plate 71 in the configuration shown, this configuration is not restrictive. For example, the groove 74 may be formed only in a distal portion of the bottom plate 71.

The outer needle 2 is held in the grooves 65 and 74, which helps prevent the outer needle 2 from coming out of position in a transverse direction in FIG. 15.

For example, the groove may be formed in only one of the pressing member 6 and the grip member 7.

Figure 16:
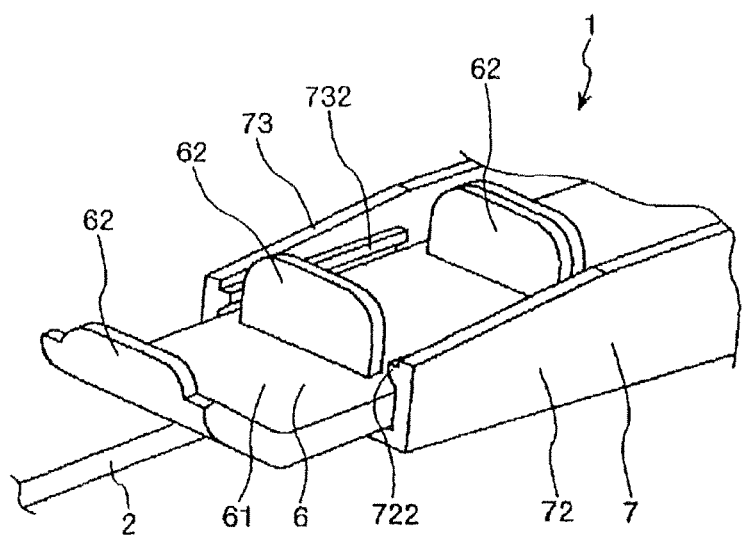
FIG. 16 is a perspective view of the pressing member and a distal portion of a grip member of the indwelling needle assembly shown in FIG. 12.

In addition, as shown in FIG. 16, ribs (engaging sections) 722 and 732 projecting sideways to engage with the pressing member 6 can be formed respectively at inner surfaces of distal portions of wall sections 72 and 73 of the grip member 7. The ribs 722 and 732 are so formed as to extend along the longitudinal direction of the grip member 7 and be parallel to each other, which helps ensures that, in the assembled state, the pressing member 6 can be prevented from being displaced in such a direction as to come away from the outer needle 2 in a radial direction of the outer needle 2. For example, the pressing member 6 can be prevented from being lifted to the upper side. As a result, the state in which the outer needle 2 is inserted in the grooves 65 and 74 is held, so that the outer needle 2 can be prevented from coming out of position in a transverse direction in FIG. 15, as above-mentioned.

By way of example, the grip member 7 has a cover section 75 which is formed at upper portions of the wall sections 72 and 73 and which covers the space on the inside of the grip member 7. In the configuration shown, the cover section 75 is provided to extend from the proximal end to the distal side relative to a middle portion, of each of the wall sections 72 and 73.

In addition, as shown in FIG. 17, the pressing member 6 can be configured to be attachable to and detachable from the outer needle hub 3. For example, a shaft 63 provided at a proximal portion of the main body section 61 of the pressing member 6 can be detachably attached to a bearing 32 provided in the outer needle hub 3. The bearing 32 is composed of a pair of C-shaped support sections 321 and 322. By way of example, the part of the proximal portion of the main body section 61 which is on the distal side of the shaft 63 can protrude in the axial direction, which helps ensure that when the pressing member 6 is positioned in the first position shown where it is disposed along the axis of the outer needle 2, the pressing member 6 cannot be detached. For example, the pressing member 6 can be prevented from being disengaged from the outer needle hub 3.

According to another embodiment, when the pressing member 6 is turned clockwise in the figure to a predetermined position relative to the outer needle 2, the pressing member 6 can be detached.

Figure 12:
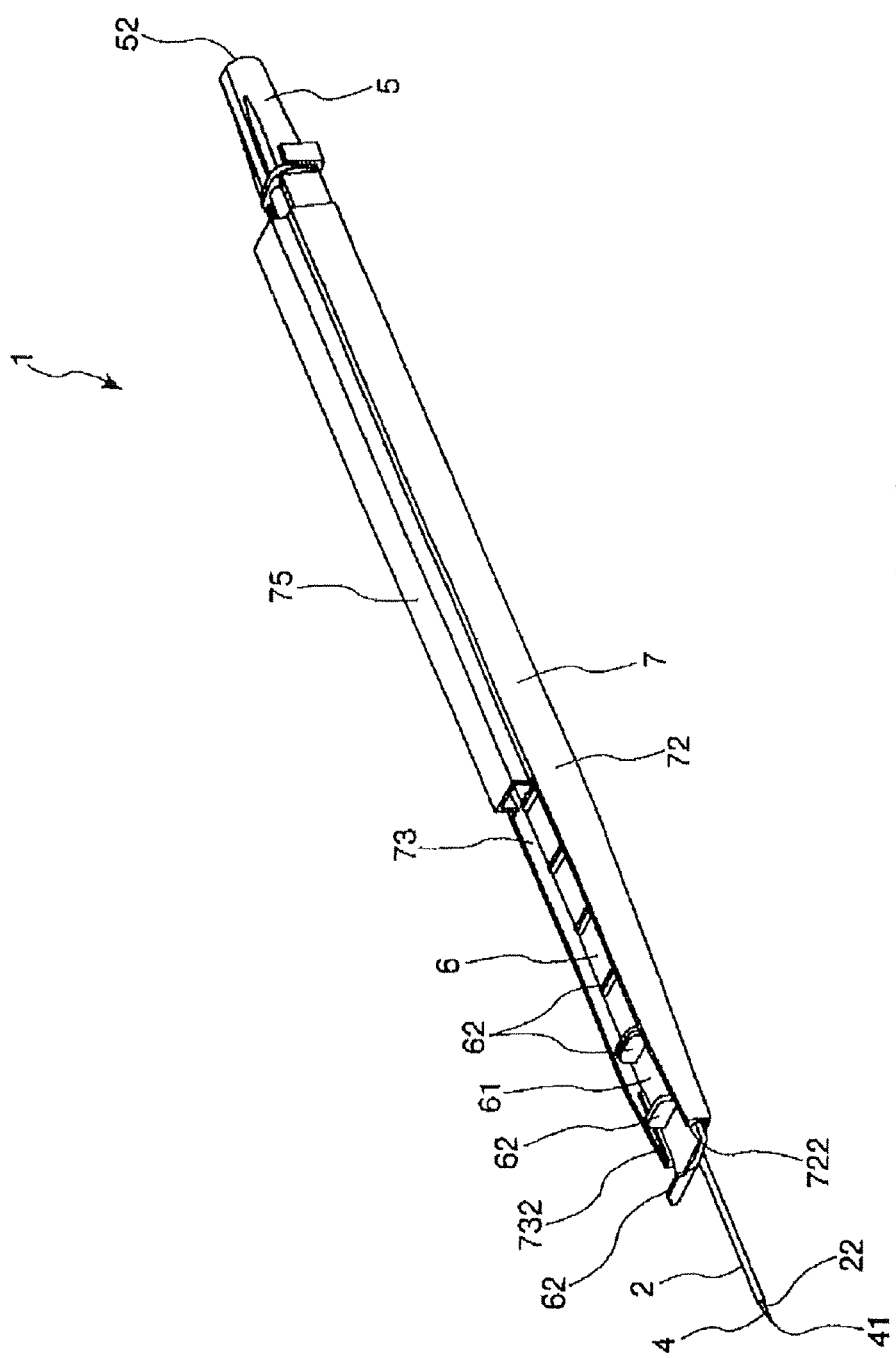
FIG. 12 is a perspective view of a third embodiment (assembled state) of an indwelling needle assembly.
Figure 13:
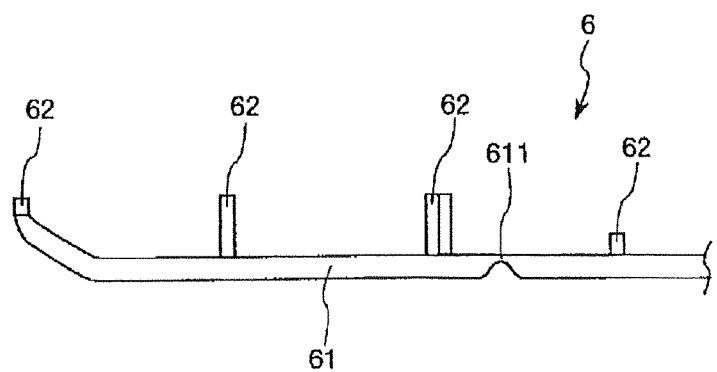
FIG. 13 is a side view of a pressing member of the indwelling needle assembly shown in FIG. 12.
Figure 17A:
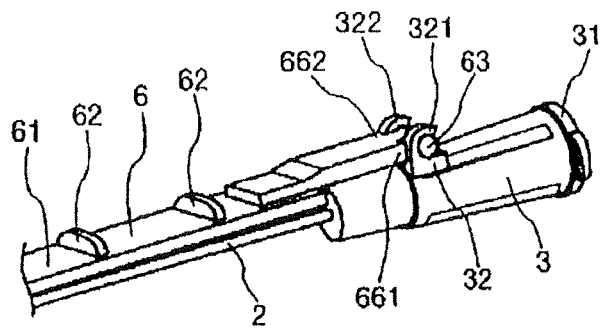
FIGS. 17a-d show perspective views of an outer needle hub and the pressing member of the indwelling needle assembly shown in FIG. 12.

The pressing member 6 has a pair of stepped sections 661 and 662 formed at that part of the main body section 61 which is on the distal side of the shaft 63, as disengagement preventive means, which helps prevent the pressing member 6 from being disengaged from the outer needle hub 3 when the pressing member 6 is positioned in the first position shown in FIGS. 12 and 17(a) where it is disposed along the axis of the outer needle 2.

The bearing 32 can have a pair of C-shaped support sections 321 and 322. The shaft 63 of the pressing member 6 is attached to and detached from the support sections 321 and 322, from and to the right side in FIG. 17.

When the pressing member 6 is positioned in the first position shown in FIG. 17(a) where it is disposed along the axis of the outer needle 2, an attempt to detach the shaft 63 from the support sections 321 and 322 by moving the pressing member 6 toward the right side in FIG. 17 fails. For example, the stepped sections 661 and 662 of the pressing member 6 come into contact with the support sections 321, 322, so that the shaft 63 cannot be detached from the support sections 321, 322. As a result, the pressing member 6 can be prevented from being disengaged from the outer needle hub 3.

Figure 17B:
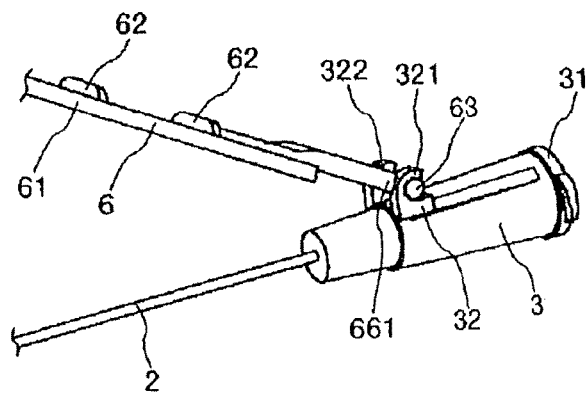

In addition, in the case where the pressing member 6 is turned clockwise in FIG. 17 from the first position, before the pressing member 6 becomes perpendicular to the outer needle 2 the shaft 63 of the pressing member 6 cannot be detached from the support sections 321 and 322, since the stepped sections 661 and 662 of the pressing member 6 abut on the support sections 321 and 322, in the same manner as above-mentioned, as shown in FIG. 17(b).

Figure 17C:
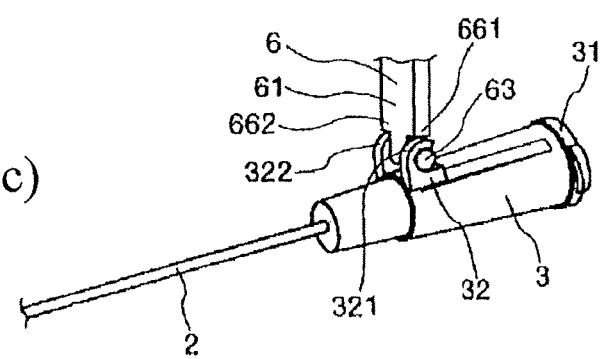
Figure 17D:
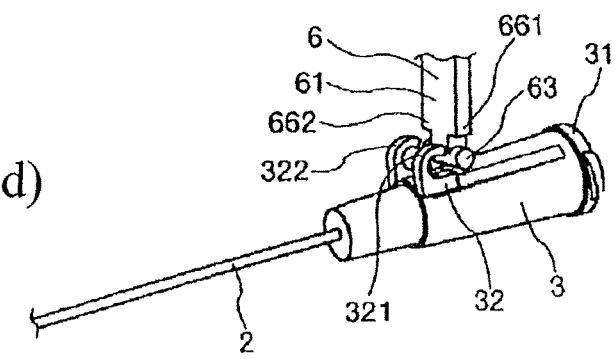

When the pressing member 6 is turned further clockwise in FIG. 17 and the pressing member 6 is turned to a predetermined position relative to the outer needle 2 as shown in FIG. 17(c), the shaft 63 of the pressing member 6 can be detached from the support sections 321 and 322, as shown in FIG. 17(d).

An example of the method of using the indwelling needle assembly 1 (in the case of puncturing a blood vessel) (operation) is disclosed below.

As shown in FIG. 12, the indwelling needle assembly 1 is put into the assembled state, and the pressing member 6 is positioned in the first position. Then, a distal portion of the grip member 7 provided at the inner needle hub 5 is gripped by one hand, and an index finger is put on the distal-most finger hook projection 62 of the pressing member 6. While pressing down the vicinity of a base portion of the finger hook projection 62 by the index finger, a distal portion of the indwelling needle assembly 1 is caused to puncture a skin of a patient toward a blood vessel, in such a manner as to press the distal portion against the patient. By way of example, the pressing section 64 presses down that part of the outer needle 2 between the proximal end and the distal end, whereby the inner needle 4 and the outer needle 2 can be restrained from deflection.

When the needlepoint 41 of the inner needle 4 has punctured the blood vessel, the internal pressure of the blood vessel causes blood to flow back in the proximal direction through the inner needle 4, to be introduced into the inner needle hub 5. This flashback can be visually confirmed through the inner needle hub 5 having visibility. As a result, it can be known that the needlepoint 41 of the inner needle 4 has securely punctured the blood vessel.

Figure 18:
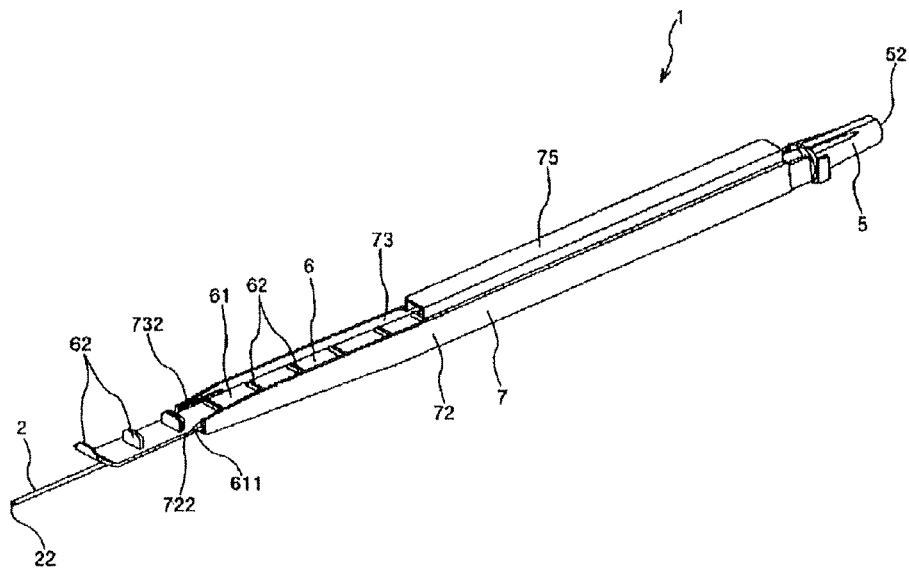
FIG. 18 is a perspective view illustrating an example of a method of using the indwelling needle assembly shown in FIG. 12.
Figure 19:
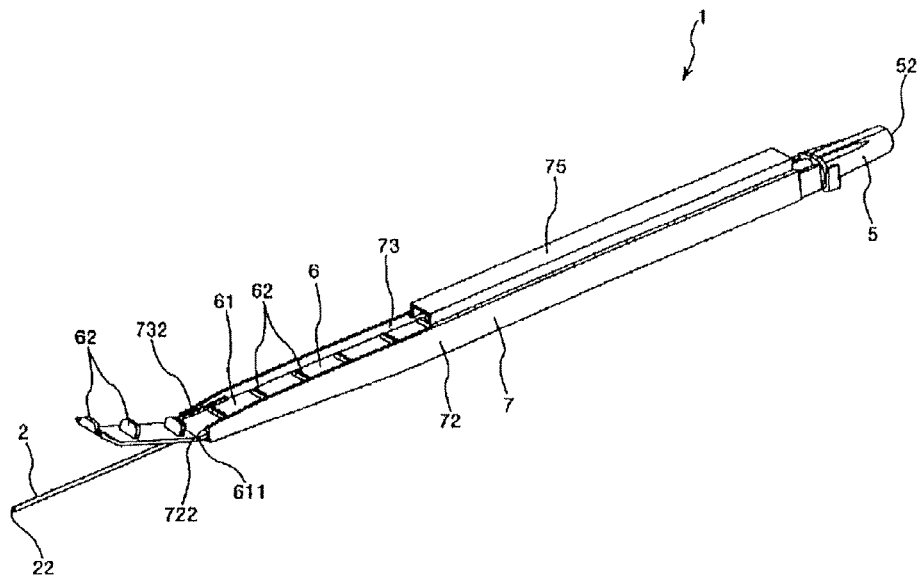
FIG. 19 is a perspective view illustrating an example of a method of using the indwelling needle assembly shown in FIG. 12.

Next, as shown in FIG. 18, the outer needle 2 is advanced further in the distal direction along the inner needle 4, with the inner needle 4 as a guide. In this instance, the distal-most finger hook projection 62 is pushed in the distal direction by an index finger, to move the outer needle 2 in the distal direction. By way of example, when the distal portion of the pressing member 6 comes into contact with a predetermined part of the patient, the pressing member 6 is curved or bent at its intermediate portion, as shown in FIG. 19, which helps ensure that the pressing member 6 would not be an obstacle, and the outer needle 2 can be moved relatively easily and smoothly.

Figure 20:
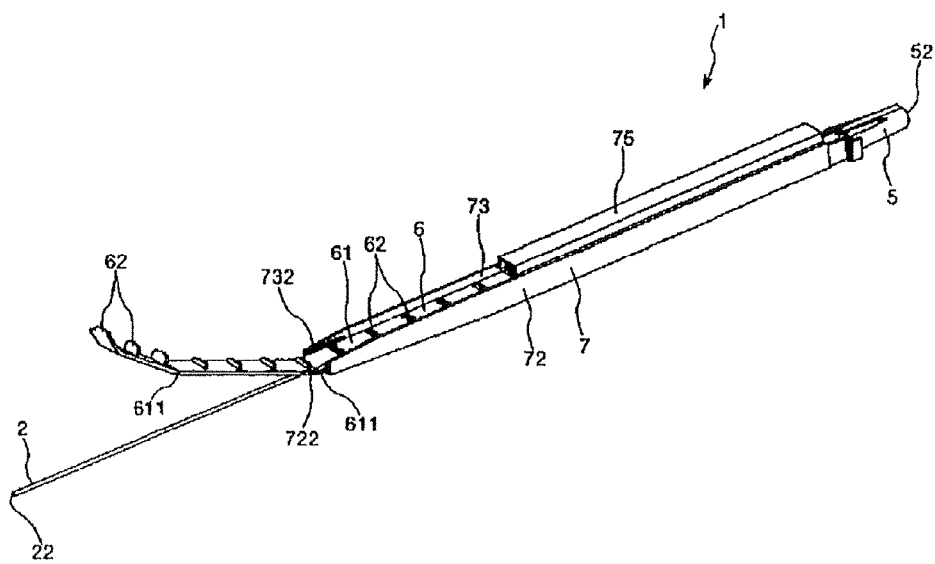
FIG. 20 is a perspective view illustrating an example of a method of using the indwelling needle assembly shown in FIG. 12.

Subsequently, as shown in FIG. 20, the second distal-most finger hook projection 62 is pushed in the distal direction by the index finger, to move the outer needle 2 in the distal direction, and such an operation is sequentially repeated to insert a distal portion of the outer needle 2 to a target position in the blood vessel. For example, when the pressing member comes into contact with the patient's predetermined part, the pressing member 6 is curved or bent at its intermediate portion, as above-mentioned. As a result, the pressing member 6 would not be an obstacle, and the outer needle 2 can be moved relatively easily and smoothly.

Figure 21:
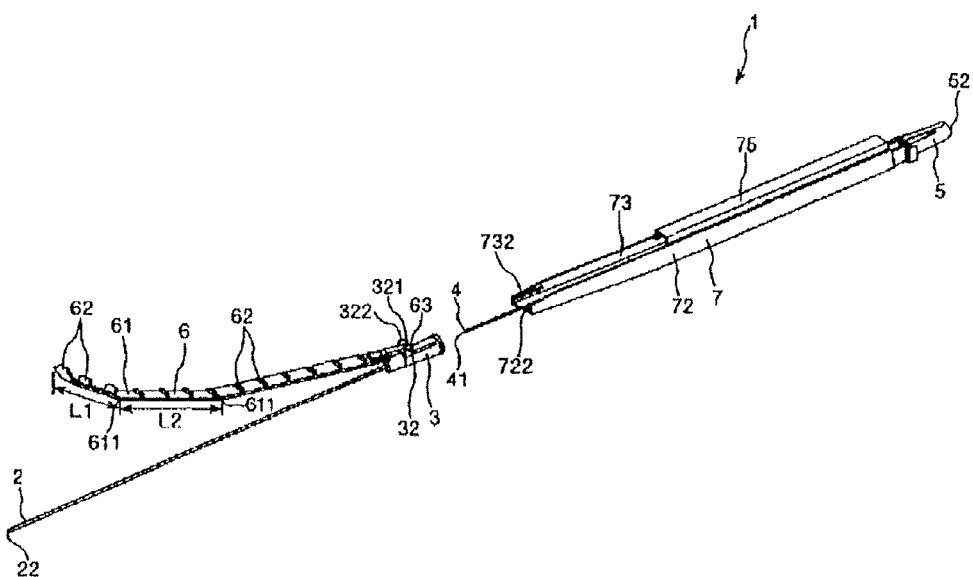
FIG. 21 is a perspective view illustrating an example of a method of using the indwelling needle assembly shown in FIG. 12.
Figure 22:
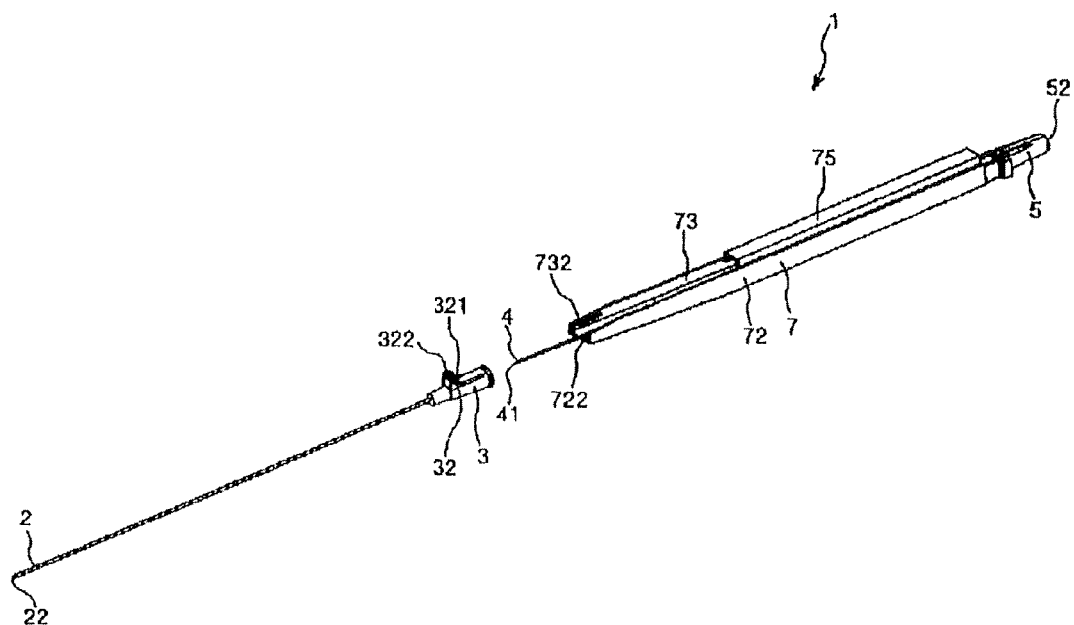
FIG. 22 is a perspective view illustrating an example of a method of using the indwelling needle assembly shown in FIG. 12.

Next, as shown in FIG. 21, while holding down by the other hand the pressing member 6 on the side of the outer needle 2 kept indwelling in the blood vessel, a proximal portion of the grip member 7 and the inner needle hub 5 are gripped and pulled in the proximal direction, which can result in the inner needle 4 pulling out of the outer needle 2. After the inner needle 4 is pulled out of the outer needle 2, if necessary, as shown in FIG. 22, the pressing member 6 may be detached from the outer needle hub 3. Alternatively, the pressing member 6 may be positioned into the second position by turning. Further, the pressing member 6 may be kept as it is. Incidentally, the subsequent operations are the same as in the second embodiment, and, therefore, descriptions of the subsequent operations are omitted.

According to this indwelling needle assembly 1, the same effects as those of the above-described second embodiment can be obtained.

Incidentally, while the main body section 61 of the pressing member 6 is formed with the small material thickness section 611 so that the pressing member 6 can be curved or bent in this embodiment, this configuration is not restrictive; for example, a hinge structure section including a shaft and a bearing for supporting the shaft may be provided at an intermediate portion in the longitudinal direction of the main body section 61 of the pressing member 6.

By way of example, in other examples, the pressing member 6 is configured to have a shape of being curved or bent at its intermediate portion in the longitudinal direction in a natural state in which no external force is exerted on the pressing member 6, and the pressing member 6 is contained in a rectilinearly stretched state in a space on the inside of the grip member 7, which helps ensures that when the restraint by the grip member 7 is released, the pressing member 6 returns into its original shape before the curving or bending, so that its interference with a predetermined part of the patient can be obviated.

In addition, while the width of the pressing member 6 has been constant in this embodiment, this is not restrictive; for example, a configuration may be adopted in which the width of the pressing member 6 is enlarged only at a distal portion, and only the distal portion of the pressing member 6 engages with the ribs 722 and 732. By way of example, when the distal portion of the pressing member 6 is located in a position corresponding to the ribs 722 and 732, the distal portion of the pressing member 6 engages with the ribs 722 and 732 whereby the distal portion is prevented from being lifted to the upper side. Then, when the pressing member 6 is moved in the distal direction and the distal portion of the pressing member 6 is located on the distal side relative to the position corresponding to the ribs 722 and 732, the pressing member 6 and the ribs 722 and 732 are disengaged from each other, so that the pressing member 6 can be moved upward. For example, the pressing member 6 can move upward before that part of the pressing member 6 on the proximal side relative to the distal portion is disengaged from the distal end of the grip member 7.

While the indwelling needle assembly disclosed here has been described above based on the embodiments shown in the drawings, the disclosure is not restricted to the embodiments, and the configuration of each component can be replaced by one of an arbitrary configuration that has the same or equivalent function to the original. Besides, an arbitrary structure or structures may be added to the configuration of the present disclosure.

In addition, the present disclosure may be embodied by a combination of arbitrary two or more of the above-described embodiments.

By way of example, the indwelling needle assembly according to the present disclosure is not limited to the one that is used in the state of being inserted into a blood vessel. The present disclosure is also applicable, for example, to those to be used in the state of being inserted into abdominal cavity, thoracic cavity, lymphatic vessel, vertebral canal or the like.

According to the present disclosure, even in the case where an inner needle and an outer needle are large in length, by pressing down that part of the outer needle between the proximal end and the distal end through a pressing member, during a puncturing operation, to restrain the inner needle and the outer needle from deflection. As a result, the puncturing operation can be carried out easily and assuredly.

In addition, the puncturing operation can be performed while putting a finger on a predetermined part of the pressing member that is nearer to the distal portions of the inner needle and the outer needle than the inner needle hub and the outer needle hub. Therefore, during the puncturing operation, the needlepoint of the inner needle can be controlled relatively easily.

The foregoing embodiments are not intended to restrict the scope of the present invention. Various changes, modifications and equivalents could be effected by one skilled in the art without departing from the spirit and scope of the invention as defined in the appended claims. It is expressly intended that all such changes, modifications and equivalents, which fall within the scope of the claims are embraced by the claims.

What is claimed is:
1. An indwelling assembly comprising:
an inner needle having a sharp needlepoint at a distal end to puncture a blood vessel of a patient when the indwelling assembly is moved toward the patient, the inner needle possessing a proximal portion;
an inner needle hub fixed to the proximal portion of the inner needle;

a hollow elongated outer member in which the inner needle is positioned, the hollow elongated outer member being movable in a distal direction relative to the inner needle after puncturing the patient's blood vessel with the sharp needlepoint to position the hollow elongated outer member at a desired position in the blood vessel, the hollow elongated outer member possessing a proximal portion;

an outer member hub fixed to the proximal portion of the hollow elongated outer member;

a main body section removably connected to the outer member hub so that the main body section is detachable from the outer member hub;

an elongated movable member that is movable relative to the hollow elongated outer member and the outer member hub, the elongated movable member being connected to the inner needle hub so that the inner needle hub, the inner needle and the elongated movable member move together, the elongated movable member projecting in the distal direction from the inner needle hub;

a cover section covering an upper side of the elongated movable member, a part of the main body section being disposed under the cover section;

the outer member hub being disposed in an area between the elongated movable member and the cover section.

2. The indwelling assembly according to claim 1, wherein the main body section includes at least one upstanding finger-contacting projection that is engageable by a user's finger to move the outer member hub, the hollow elongated outer member and the main body section in the distal direction.

3. The indwelling assembly according to claim 2, wherein the main body section possesses a distal end and a proximal end, and the at least one upstanding finger-contacting projection is positioned closer to the distal end of the main body section than the proximal end of the main body section.

4. The indwelling assembly according to claim 1, wherein the main body section is removably connected to the outer member hub by way of at least one projecting part of the main body section engaging a part of the outer member hub.

5. The indwelling assembly according to claim 1, wherein a portion of the main body section overlies a portion of the outer member hub, the main body section being removably connected to the outer member hub by way of at least one projecting part of the main body section engaging a part of the outer member hub.

6. The indwelling assembly according to claim 1, wherein a portion of the main body section is exposed outside the cover section before puncturing the patient's blood vessel with the sharp needlepoint.

7. The indwelling assembly according to claim 1, wherein the elongated movable member and the main body section are relatively movable so that the elongated movable member and the main body section are completely separable from one another.

8. The indwelling assembly according to claim 1, wherein the elongated movable member includes two spaced apart side walls projecting upwardly from a bottom portion of the elongated movable member, the side walls possessing an upper edge, the main body section including an upstanding finger-contacting projection that is engageable by a user's finger to simultaneously move the outer member hub, the hollow elongated outer member and the main body section in the distal direction, the finger-contacting projection possessing an upper surface, the upper surface of the finger-contacting projection being located above the upper edge of each of the side walls of the elongated movable member.

9. An indwelling assembly comprising:
an inner needle having a sharp needlepoint at a distal end to puncture a blood vessel of a patient when the indwelling assembly is moved toward the patient, the inner needle possessing a proximal portion;

an inner needle hub fixed to the proximal portion of the inner needle so that the inner needle and the inner needle hub move together as a unit;

a hollow elongated outer member in which the inner needle is positioned, the hollow elongated outer member being movable in a distal direction relative to the inner needle after puncturing the patient's blood vessel with the sharp needlepoint to position the hollow elongated outer member at a desired position in the blood vessel, the hollow elongated outer member possessing a proximal portion;

an outer member hub fixed to the proximal portion of the hollow elongated outer member so that the hollow elongated outer member and the outer member hub move together as a unit;

an elongated movable member connected to the inner needle hub so that movement of the elongated movable member results in movement of the inner needle hub and the inner needle, the elongated movable member including two spaced apart side portions projecting upwardly away from a bottom portion so that the two side portions and the bottom portion together define a space, the elongated movable member projecting in the distal direction from the inner needle hub, the inner needle being positioned in the space before puncturing the patient's blood vessel, a main body section connected to the outer member hub so that the main body section and the outer member hub move together, the main body section being detachable from the outer member hub, a part of the main body section overlying the outer member hub;

a cover section overlying a part of the space in the elongated movable member and also overlying a section of the main body section positioned in the space so that the section of the main body section is positioned between the bottom portion of the elongated movable member and the cover section; and a portion of the main body section being uncovered by the cover section before puncturing the patient's blood vessel so that the portion of the main body section is engageable by a user's finger to move the hollow elongated outer member in the distal direction relative to the inner needle after puncturing the patient's blood vessel to thereby position a distal end of the hollow elongated outer member distally beyond the sharp needlepoint.

10. The indwelling assembly according to claim 9, wherein a portion of the outer member hub is positioned in the space, the cover section overlying the portion of the outer member hub that is positioned in the space.

11. The indwelling assembly according to claim 9, wherein the portion of the main body section that is uncovered by the cover section includes at least one upstanding finger-contacting projection that is engageable by the user's finger to move the outer member hub, the hollow elongated outer member and the main body section in the distal direction.

12. The indwelling assembly according to claim 11, wherein the main body section possesses a distal end and a proximal end, and the at least one upstanding finger-contacting projection is positioned closer to the distal end of the main body section than the proximal end of the main body section.

13. The indwelling assembly according to claim 11, wherein the main body section is detachable from the outer member hub by virtue of the main body section being removably connected to the outer member hub, the main body section being removably connected to the outer member hub by way of at least one projecting part of the main body section engaging a portion of the outer member hub.

14. The indwelling assembly according to claim 11, wherein an overlying part of the main body section overlies a part of the outer member hub, the main body section being removably connected to the outer member hub by way of at least one projecting part of the main body section engaging a portion of the outer member hub.

15. The indwelling assembly according to claim 11, wherein the elongated movable member and the main body section are relatively movable so that the elongated movable member and the main body section are completely separable from one another in which the main body section is entirely outside the space.

16. The indwelling assembly according to claim 9, wherein the two side portions each possess an upper edge, the main body section including an upstanding finger-contacting projection that is engageable by a user's finger to simultaneously move the outer member hub, the hollow elongated outer member and the main body section in the distal direction, the finger-contacting projection possessing an upper surface, the upper surface of the finger-contacting projection is located above the upper edge of each of the two side portions of the elongated movable member.

* * * * *